(12) United States Patent
Torres et al.

(10) Patent No.: US 7,851,226 B2
(45) Date of Patent: *Dec. 14, 2010

(54) OSMOTIC REACTION DETECTOR FOR MONITORING BIOLOGICAL AND NON-BIOLOGICAL REACTIONS

(75) Inventors: Francisco E. Torres, San Jose, CA (US); Karl Littau, Palo Alto, CA (US); Eric Shrader, Belmont, CA (US)

(73) Assignee: Xerox Corporation, Norwalk, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/546,713

(22) Filed: Aug. 25, 2009

(65) Prior Publication Data

US 2009/0320573 A1    Dec. 31, 2009

Related U.S. Application Data

(62) Division of application No. 10/739,852, filed on Dec. 18, 2003, now Pat. No. 7,615,375.

(51) Int. Cl.
*G01N 7/00* (2006.01)

(52) U.S. Cl. ............... 436/148; 436/43; 422/50; 422/68.1; 422/81; 422/82.01; 73/1.01; 73/1.02; 73/53.01; 73/47; 73/78

(58) Field of Classification Search .......... None
See application file for complete search history.

(56) References Cited

U.S. PATENT DOCUMENTS

| | | |
|---|---|---|
| 3,195,346 A | 7/1965 | Ehrmantraut et al. |
| 3,737,045 A | 6/1973 | Hashimoto |
| 4,028,931 A | 6/1977 | Bisera et al. |
| 4,111,203 A | 9/1978 | Theeuwes |
| 4,455,864 A | 6/1984 | Wallner |
| 4,475,556 A | 10/1984 | Reiff |
| 5,005,403 A | 4/1991 | Steudle et al. |
| 5,141,873 A | 8/1992 | Steudle et al. |
| 5,189,917 A | 3/1993 | Vijayakumar et al. |
| 5,279,793 A | 1/1994 | Glass |

(Continued)

FOREIGN PATENT DOCUMENTS

FR    2672994    8/1992

(Continued)

OTHER PUBLICATIONS

Reomer, et al., "Microactuators Based On Conducting Polymers", Analytical Bioanalytical Chemistry, 2002, vol. 373, pp. 754-757.

(Continued)

*Primary Examiner*—Yelena G Gakh
*Assistant Examiner*—Robert Xu
(74) *Attorney, Agent, or Firm*—Fay Sharpe LLP

(57) ABSTRACT

A method and apparatus for measuring the presence or absence of reaction between a first and second material of interest by measuring osmotic pressure changes in a reaction cell. The reaction cell is capable of measuring the small changes in pressure that occur due to osmotic pressure shifts during a catalytic or binding reaction at species concentrations down to approximately $10^{-7}$ M.

18 Claims, 7 Drawing Sheets

U.S. PATENT DOCUMENTS

| | | | |
|---|---|---|---|
| 5,337,747 | A | 8/1994 | Neftel |
| 5,388,449 | A | 2/1995 | LeVeen et al. |
| 5,665,904 | A | 9/1997 | Boling |
| 6,267,003 | B1 | 7/2001 | Boris |
| 6,268,161 | B1 | 7/2001 | Han et al. |
| 6,597,499 | B2 | 7/2003 | Kawano et al. |
| 7,017,394 | B2 | 3/2006 | Sullivan |
| 7,141,210 | B2 | 11/2006 | Bell et al. |
| 7,553,669 | B2 | 6/2009 | Torres et al. |
| 2004/0258753 | A1 | 12/2004 | Demeester et al. |
| 2005/0130319 | A1 | 6/2005 | Biegelsen et al. |
| 2005/0136543 | A1 | 6/2005 | Torres et al. |
| 2006/0134601 | A1 | 6/2006 | Torres et al. |
| 2008/0118985 | A1 | 5/2008 | Torres et al. |

FOREIGN PATENT DOCUMENTS

| | | | |
|---|---|---|---|
| JP | 02226045 | A | 9/1990 |
| WO | 03061475 | A1 | 7/2003 |

OTHER PUBLICATIONS

Bourdillon, "An Apparatus For The Rapid And Accurate Determination Of Low Osmotic Pressures", Journal of Biological Chemistry, 1939, vol. 127, pp. 617-625.

Wentworth, et al., "Catalytic Antibodies: Structure And Function", Cell Biochemistry And Biophysics, 2001, vol. 35, pp. 63-87.

Homola, et al., "Surface Plasmon Resonance Sensors: Review", Elsevier Science S.A., Sensors And Actuators, 1999, B 54, pp. 3-15.

Homola et al., "Present And Future Of Surface Plasmon Resonance Biosensors", Analytical And Bioanalytical Chemistry, Oct. 2003, vol. 377, No. 3, pp. 528-529.

Jung, et al., "Quantitative Interpretation Of The Response Of Surface Plasmon Resonance Sensors To Adsorbed Films,", American Chemical Society, Langmuir, 1998, 14, pp. 5636-5648.

Haemers, et al., "An Alternative Method To Quantify Surface Plasmon Resonance Measurements Of Adsorption On Flat Surfaces", American Chemical Society, Langmuir, 2002, 18, pp. 2069-2074.

Mamishev, et al., "Interdigital Sensors And Transducers", Proceedings Of The IEEE, May 2004, vol. 92, No. 5, pp. 808-845.

Quake, et al., "From Micro- To Nanofabrication With Soft Materials", Science, Issues In Nanotechnology, Nov. 24, 2000, vol. 290, pp. 1536-1540.

Pelrine et al., "High Speed Electrically Actuated Elastomers With Strain Greater Than 100%", Science, Feb. 4, 2000, vol. 287, pp. 836-839.

OSMOTIC REACTION DETECTOR FOR MONITORING BIOLOGICAL AND NON-BIOLOGICAL REACTIONS

INCORPORATION BY REFERENCE

This is a divisional of application of U.S. Patent Publication No. 2005-0136543-A1, published Jun. 23, 2005, entitled "Osmotic Reaction Detector For Monitoring Biological And Non-Biological Reactions", by Francisco E. Torres et al., the disclosure of which is hereby incorporated by reference in its entirety.

BACKGROUND

The present exemplary embodiments relate to monitoring reactivity in biological and non-biological reactions. It finds particular application in conjunction with the reactivity between materials in an array, such as a microarray or array of wells of a microtitre plate, and will be described with particular reference thereto. However, it is to be appreciated that the present exemplary embodiments are also suitable for use in monitoring in non-array environments as well.

Researchers are increasingly employing combinatorial chemistry techniques in a variety of areas. In the pharmaceutical industry, the testing of new candidate molecules for binding to a protein, nucleic acid, or other macromolecules of interest is an active area of research with numerous and diverse applications. In addition, there is a great interest in developing new antibodies to catalyze the formation of novel compounds, to catalyze the degradation of unwanted compounds, to modify biological pathways, and to act as therapeutic agents for drug overdose, biological warfare agent exposure, and other conditions caused by particularly potent antigens and poisons.

To test the reactivity in both binding and catalytic reactions of these molecules, researchers are using various techniques, including microarrays and "lab-on-a-chip" type devices. In such techniques, researchers can rely on fluorescent tags to test for reactions between subject molecules. While effective, fluorescent tags must be attached to each candidate compound prior to testing. This process is cumbersome and makes the testing of large numbers of samples time consuming. The article "Catalytic Antibodies: Structure and Function", P. Wentworth and K. Janda (Cell Biochemistry and Biophysics, vol. 35, pp. 63-87, 2001) illustrates many of the problems faced, and gives examples of procedures followed by researchers employing combinatorial chemistry techniques to develop new antibodies.

One technique that researchers are using for real-time, high-throughput monitoring of fast reactions relies on nanocalorimetry-based processes, such as described in commonly assigned U.S. Pat. No. 714,210 issued Nov. 28, 2006 to Bell, and titled "Apparatus and Method for a Nanocalorimeter for Detecting Chemical Reactions", hereby incorporated by reference. While effective for samples where the reaction produces sufficient heat in a time scale normally on the order of up to several to tens of seconds, nanocalorimetry is not suitable in applications where the reaction is too slow or too weak to produce a detectable heat. This problem is especially pronounced for those reactions which may require minutes or even hours.

In investing alternatives, it has been appreciated that osmotic pressure may provide a useful measurement. Particularly, it is known that the osmotic pressure of a solution is a colligative property that depends on the concentration of solute molecules in the solution. For dilute solutions, the osmotic pressure Π obeys the equation Π=cRT, where c is molar concentration of solute, R is the gas constant, and T is the absolute temperature. Essentially, each mole of solute contributes RT thermal energy to the osmotic pressure.

In a biological test for reaction between a first material and second material of interest, e.g., a protein, and a candidate "probe" compound (or ligand), consider the case where both species are initially present in the same molar concentration, N, in a reaction cell. The use of the terms "first material" and "second material" may be used interchangeably herein with the terms "material 1" and "material 2", respectively, and are intended to be synonymous unless specifically stated. In this initial, unreacted state, the combined concentration of both species is 2 N, and each species contributes equally to the osmotic pressure in the cell. If the first material reacts with the second material to form a bound complex molecule, then N moles per unit volume of the first material reacts with N moles per unit volume of the second material to produce N moles per unit volume material 1-material 2 complex. Accordingly, the osmotic pressure due to these two components drops to ½ its previous level prior to binding.

Conversely, if the reaction of interest is catalytic in nature, for example in the case of a catalytic antibody reaction with an antigen in which the catalytic antibody cleaves the antigen, then N moles per unit volume of material 1 react with N moles per unit volume of material 2 to form 2 N moles per unit volume material 2 fragments plus the original N moles per unit volume of material 1. In this case, the osmotic pressure increases by ½. The osmotic pressure is also a parameter which may be monitored over an extended period of time, such as, for example, for up to several hours.

There have therefore been attempts to use osmotic pressure to test for reactivity in both biological systems. However, these systems have generally examined high concentration environments in which the osmotic pressure is no less than approximately 5,000 to 10,000 N/m². Furthermore, previous systems typically tested for only a single reaction at a time.

In many cases, however, it is desirable to undertake studies at low concentrations, which will generate osmotic pressures at levels much lower than present osmotic-based systems are capable of detecting. One reason the use of low concentrations is attractive, is that the materials may be scarce and/or expensive, making use of larger concentrations impossible or cost prohibitive. Additionally, the quantity of experiments may require the use of low concentrations. In drug screening experiments, for example, researchers may be running anywhere from 1,000 to 100,000 or more different experiments. The use of large concentrations of materials would significantly increase the cost to such a large number of experiments.

Another benefit of low concentration studies is that the use of smaller concentrations provides for more selective reactions. Consider, for example, the

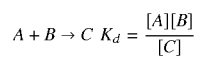

study of a binding reaction with a dissociation constant $K_d$:

In this reaction, A and B bind to form the complex C, and the dissociation constant is written in terms of concentrations denoted by square brackets. This equation assumes ideal solution behavior, but it is sufficient for the purposes herein. In testing for binding, it is often desired to obtain an indication of the magnitude of $K_d$. In many biochemical studies, including drug screening and development studies and proteome-wide investigations of protein-protein interactions, among others, $K_d$ values of interest are typically <1-10 μM, and values from 1-1000 nM—and especially <100 nM—are not uncommon and often of particular interest. In order to measure $K_d$, the reaction must be studied at concentrations that are not too distant from the value of $K_d$. At the upper end of this range, titrations may be performed at concentrations of 10 to 100 times $K_d$, but titrations at concentrations near the value of $K_d$ are preferred when possible. Thus, there is a benefit to performing studies at as low a concentration as possible. In particular, there is a benefit to being able to perform studies at concentrations as low as $10^{-6}$ to $10^{-7}$ M. Likewise, it is a benefit to be able to measure kinetics of enzymatic reactions at low concentrations, including enzymatic reactions with slow turnover rates.

Upon a review of the state of art, it has been determined that there are no direct, simple, and generic assay techniques or systems for testing large numbers of samples of interest at the low concentration levels of interest. Available techniques require tagged molecules (e.g. for fluorescent, colorimetric, spectrophotometric, or radiolabelled tags), immobilization of reactants at or near a surface, antibody-based affinity screens, or other specific preparations that either modify the reacting molecules or are otherwise specific to the particular compounds being tested.

BRIEF DESCRIPTION

In accordance with a first aspect of the present exemplary embodiments, a method for monitoring reactivity in reactions between a first and second material of interest is provided, the method including the steps of providing an osmotic reaction cell including first and second wells and a semi-permeable membrane separating the first and second wells; introducing a reference solution comprising any one or combination of the first material of interest, the second material of interest, a surrogate reference material and a carrier fluid into one of said first well and said second well; introducing a reaction mixture into one of the first well or the second well, which does not contain the reference solution, the reaction mixture comprising a carrier fluid and the first and second materials of interest; and monitoring a change in an osmotic pressure in said osmotic reaction cell occurring as a result of a change in concentration in said osmotic reaction cell of one or more of said first material, second material, surrogate reference material or reaction products formed from said first and second materials.

In accordance with a second aspect of the present exemplary embodiments, an osmotic cell system for monitoring reactivity in reactions between first and second materials of interest is provided, the osmotic cell system including a first well for containing one of a reference solution and a reaction mixture including first and second materials of interest; a second well for containing the other of the reference solution and the reaction mixture; a semi-permeable membrane separating the first well from the second well; and a pressure sensor for measuring changes in osmotic pressure in one of the first well and the second well.

In accordance with a third aspect of the present exemplary embodiments, a method for monitoring reactions is provided, the method including measuring osmotic pressure changes in a reaction cell including first and second wells and a semi-permeable membrane; the reaction cell containing a reference solution and a reaction mixture, wherein the method of measuring includes measuring the osmotic pressure changes as low as 1.2 N/m².

In accordance with a fourth aspect of the present exemplary embodiments, a method for monitoring reactions is provided, the method including measuring osmotic pressure changes in individual reaction cells positioned in an array of parallel reaction cells, each reaction cell including first and second wells and a semi-permeable membrane; the reaction cells each containing a reaction mixture and a reference solution, wherein the method of measuring includes measuring said osmotic pressure changes as low as 1.2 N/m².

DETAILED DESCRIPTION

As used herein, the terms "first material" and "second material" as well as "material 1" and "material 2" are meant to refer broadly to any two compounds or molecules, of which the potential reactivity between the two is of interest to an investigator. Thus, the terms may refer to without limitation any protein, peptide, polypeptide, nucleic acid, oligonucleotide, compounds bound to beads or matrix materials, antigens or other species that may react therewith. In the present discussion, then, reference will at times be made to an antibody and an antigen as the first and second materials. The reactions that such species will undergo include catalytic antibody reactions and antibody binding, among others.

It is to be understood that the first and second materials are not to be construed as limited to the recited materials but are intended to encompass all materials which may be understood to be usable with the described methods and devices. In addition, it should be understood that that the present methods and apparatuses can be used with more than two materials of interest so long as the concentration per unit volume changes during reaction between the materials. For convenience and clarity, the focus of the herein described embodiments relate particularly to biological reactions such as, for example, those involving antibodies and antigens, proteins and ligands, proteins and other proteins, and nucleic acids. Therefore, specific reference may be made to the use of an antibody and an antigen as the first and second materials. It is, however, to be understood this is not intended to limit the disclosed concepts to these specific biological reactions, but rather the disclosure may also pertain to other biological as well as non-biological reactions.

Exemplary embodiments described herein relate to sensors including one or more reaction cells or reaction detectors, and methods for measuring changes in osmotic pressure that may occur during a reaction between two or more materials, including catalytic and binding reactions. When more than a single reaction cell or detector is present, the sensor may be thought of as an array of reaction cells or detectors. It is of course to be appreciated, however, that the same principles relate equally to a single reaction cell or detector.

Figure 1:
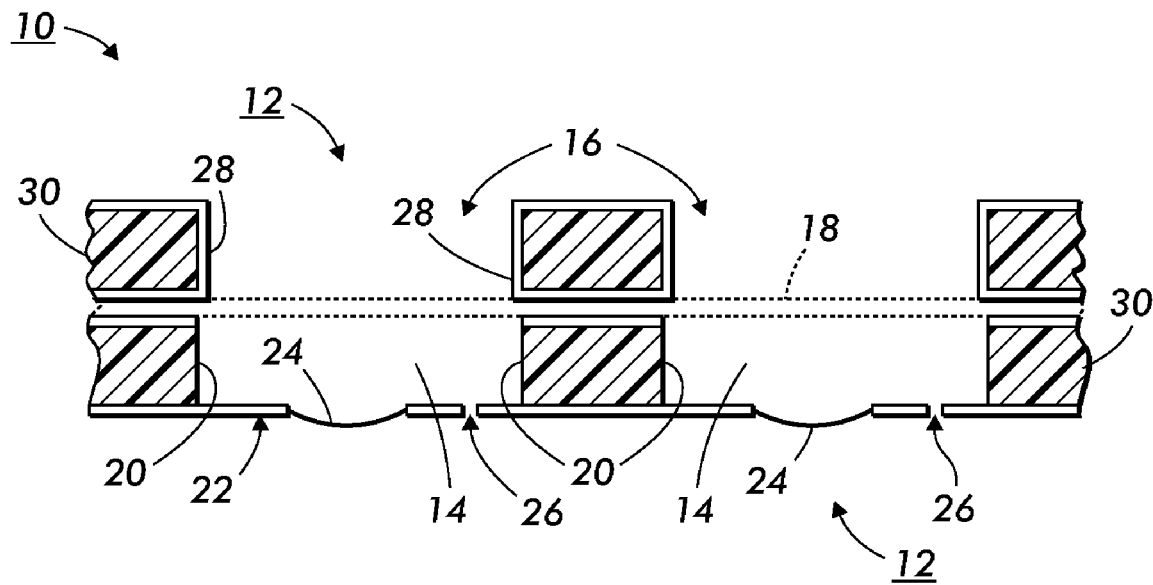
FIG. 1 is a side view of an array of empty osmotic reaction cells according to one embodiment.

With reference to FIG. 1, in a first embodiment, a sensor 10 includes osmotic reaction cells 12, each including enclosed lower or first wells 14 and upper or second wells 16 separated by a semi-permeable membrane 18. Each first well 14, includes side walls 20, and a bottom surface 22 defining an opening. A flexible diaphragm 24 is fabricated in or otherwise disposed in the opening provided in bottom surface 22. The side walls 20, bottom surface 22, and flexible diaphragm 24, together form an interior chamber into which fluid is introduced via a fluid input 26. Second wells 16 are defined by side walls 28 and the semi-permeable membrane 18, which forms a bottom surface of the second wells 16. The upper end of second wells 16 is shown to be open to permit the introduction of fluid. The reaction cells 12, continue to the left and to the right 30, as shown in the figure, when the cells 12 are part of a large array of osmotic cells.

It is to be appreciated the configuration of the sensor 10 of FIG. 1 may be altered and will nevertheless still fall within the concepts of the exemplary embodiments. For example, fluid input 26 may be arranged in any of a number of well known designs, such as a check valve or one way valve, to ensure fluid provided to each lower well 14 is maintained within the well. Also, the upper end of second wells 16 may be enclosed, and a fluid input, such as 26 of first wells 14, will permit the introduction of fluid. Still further, although FIG. 1 shows the semi-permeable membrane 18 as continuous and extending through the walls 20 of the reaction cells 12, such an arrangement is not required in this embodiment, and the semi-permeable membrane 18 may instead be discontinuous and extend only between the walls of the reaction cells 12.

Figure 2:
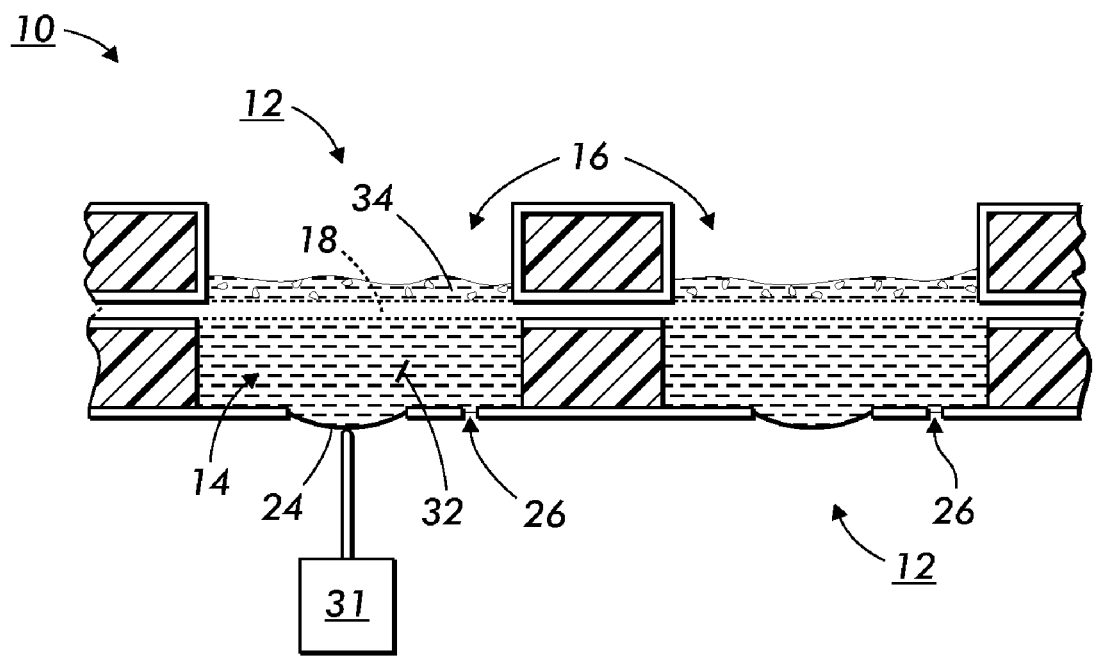
FIG. 2 is side view of an array of filled osmotic reaction cells of FIG. 1.

In one embodiment of operation, as shown in FIG. 2, the first wells 14 are filled through the input 26 with a reference solution 32 containing a carrier fluid and a reference material. This reference material can be a material of interest of which the level of reactivity with a second material of interest is desired to be known, such as an antibody. Alternately or in addition to this material of interest, the reference material may be a surrogate material that is non-reacting either with itself or with other solutes (if present) in the reference solution at the desired concentration. What is desired in the reference solution is a solution having a total number of solute molecules that will not change. Alternately, the reference material may only contain a carrier fluid, without any reference material or other solutes dissolved therein. For the following discussion, the reference material will be described as being an antibody, although any other non-reacting material is also suitable as discussed above.

After equilibrium has been reached, the pressures in the first wells 14 is recorded, by any known detection system 31, to calibrate the sensor. More detailed discussions of selected detection systems are provided in subsequent sections herein. As appreciated by those skilled in the art, the identity of the carrier fluid will vary depending on the identity of the antibody. However, the carrier fluid is chosen whereby the antibody is at least partially soluble in the carrier fluid at conditions (e.g. temperature, etc.) under which testing will be carried out.

Subsequently, a reaction mixture 34 containing a carrier fluid as well as both an antibody and an antigen species is introduced into the second wells 16 of the reaction cells. The carrier fluid in the reaction mixture 34 and the reference solution 32 may commonly be the same. As an example that is useful for illustrative purposes but is not intended to be requiring the same for practice of the invention, embodiments are discussed herein in which the total antibody and antigen concentration in the second wells 16 matches (i.e. is equal to) the antibody concentration in the first wells 14. It is to be appreciated however, that the concentration in the first wells 14 and second wells 16 do not need to match. For example, particularly if a site (or well) is used as reference site (or well) the concentrations need not be equal.

Additionally, while in the above example, the first wells 14 are filled with reference solution 32, and the second wells 16 are filled with reaction mixture 34, an opposite filling of the wells may at times be appropriate, where the first wells are filled with the reaction mixture 34 and the second wells 16 are filled with the solution 32.

The amount of solution in both the first and second wells is selected based on the size of the wells as well as other considerations. The embodiments described herein are well suited to test for reactions at reactant concentrations of preferably in the range of approximately $5 \times 10^{-5}$ to $10^{-7}$ M, and more preferably down to approximately $5 \times 10^{-6}$ to $10^{-7}$ M, assuming a solution amount of approximately 0.1 microliters to 100 microliters. Thus, in an exemplary embodiment, the wells may be approximately 1 mm on a side and approximately 100 microns deep for a total volume of 0.1 μl. Of course, the embodiments should not be construed as being limited to such ranges or geometric shapes, and the principles of operation can be applied to larger or smaller wells, solution amounts, and concentrations of species therein. In the presently described embodiments, the volume of each well is typically from about 0.05 μl to about 100 μl.

In keeping with the spirit of the embodiments, however, the size of the cells and amount of fluid are appropriately selected based on the pressure levels to be sensed. Therefore, the disclosed components and the fluid amounts are matched to provide a temperature equilibrium across the fluid in the wells, whereby an undesirable temperature gradient is avoided which might otherwise result in inaccurate measurements of volumes of interest.

Each reaction cell may be filled via any known method, such as through the use of micropipets or any other fluid delivery system. One method contemplated by the inventors is through the use of a delivery system similar to that used in high end ink jet printing devices including acoustic drop ejection systems. Such systems are known in the art and may be readily adapted for use with the exemplary embodiments of present embodiments. For example, when the second wells 16 in are open, then it is straightforward to use commercially available, robotic liquid sample delivery systems to deliver samples to these chambers. In an array application, sometimes all of the first wells 14 will contain the same solution, in which case a closed liquid delivery system can be used to deliver sample to all chambers With continuing reference to FIG. 2, the semi-permeable membrane 18 is selected such that it is permeable to the carrier fluid, but impermeable to the antibody, the antigen, and any reaction products formed between the two. As mentioned above, for illustrative purposes the case is considered where the total antibody and antigen concentration in the second wells 16 matches the antibody concentration in the first wells 14. For this choice of concentration, when there is no reaction between the antibody and the antigen, then the difference in osmotic pressure between a first and second well is negligible or zero. In that case, with the upper or second well at atmospheric pressure, the lower or first well also tends toward that same pressure, after the gravitational effect on pressure is taken into account for the height of the liquid. Suitable membranes are known in the art and include, for example, various dialysis membranes available from, among others, Fisher Scientific. These membranes have, for example, molecular weight cutoffs ranging from 100 Dalton to 300,000 Dalton, which are appropriate for the ranges and types of reactants described herein.

In an alternate embodiment, the semi-permeable membrane does not need to be impermeable to all components in both the first and second materials as well as products formed therefrom. Rather, the present embodiments can be used to determine the occurrence and extent of reaction between the first and second materials so long as the molar concentration of impermeable components changes when a reaction in the reaction cell occurs. For example, it may be the case where a catalytic antibody reacts with an impermeable molecule, breaking it up into parts that are all permeable. In such a case, there are permeable products, but the number of impermeable components changes from two (i.e. the catalytic antibody plus the impermeable molecule) to one (catalytic antibody). This reaction would give a change in osmotic pressure. This is also the case for a reaction that changes permeable reactants into impermeable products. On the other hand, if a catalytic antibody cleaved an impermeable reactant into two separate molecules, one permeable and the other impermeable, then there would not be a shift in osmotic pressure because the molar concentration of impermeable entities would not change.

Conversely, any binding or catalytic reaction between the antibody and the antigen alters the number of total solute molecules in the second well when both species are impermeable, which in turn changes the osmotic pressure difference between the first and second wells in a reaction cell 12. For example, and with initial concentrations as described above, if the antigen and antibody undergo a binding reaction to form an antigen-antibody complex molecule, then N moles per unit volume of the antigen compound react with N moles per unit volume of antibody to produce N moles per unit volume of antigen-antibody complex. Accordingly, the osmotic pressure due to these two components drops to ½ its previous level. This results in the osmotic pressure in the first well (containing antibody at concentration 2 N and no antigen) being larger than the osmotic pressure in the second well, since the antibody concentration in the first well is twice that of the antigen-antibody complex of the second well after the reaction.

An opposite result occurs if there is a catalytic reaction between the antigen and the antibody in the second well that cleaves the antigen. In this case, N moles per unit volume of antigen molecule may react with N moles per unit volume of antibody to form 2 N moles per unit volume of antigen fragments plus the original N moles per unit volume of catalytic antibody, increasing the osmotic pressure in the second cell and resulting in the osmotic pressure in the first well being smaller than the osmotic pressure in the second well. It should be noted that the above description assumes equal molar concentrations for both the antibody and the antigen. This is not necessary, however, and the described embodiments can readily be extended to systems for which the molar concentrations of antibody and antigen are unequal. In such a case, there would be a need for suitable calibration or comparison with osmotic pressure in one or more reference cells.

As previously noted, these osmotic pressure changes due to reactions between the antigen and the antibody are defined by the equation:

$$\Pi = cRT,$$

where $\Pi$ is osmotic pressure, c is molar concentration of solute, R is the gas constant, and T is the absolute temperature. When the reaction is carried out in sensor 10 described above, these differential pressure changes manifest themselves in a deflection of the flexible diaphragm 24. The present embodiments are particularly well-suited to measure osmotic pressure changes for reactions in which the species are initially present in concentrations in a range of approximately $5 \times 10^{-5}$ to $5 \times 10^{-7}$ M. At these concentrations, $\Pi$ typically ranges from about 1.2 to 130 N/m$^2$, based on typical measurement temperatures in the range of 5° C. to 40° C. The embodiments are, however, also compatible with solutions having higher concentrations as well.

To measure such small pressure changes, the diaphragm preferably has an inherent spring constant such that the deflection of the diaphragm in response to osmotic pressure changes can be detected. The deflection of an exemplary diaphragm can be predicted using Roark's formula for a circular diaphragm fixed and held at the edges undergoing large deformation:

$$\frac{l^4 P}{E t^4} = \frac{5.33}{1-v^2}\frac{y}{t} + \frac{2.6}{1-v^2}\left(\frac{y}{t}\right)^3$$

In this equation, y is the deflection, l is the radius of the diaphragm, P is the pressure, E is Young's modulus (which are typically in the range of 0.3-10 MPa for typical electroactive polymer diaphragm materials of interest as described below), v is Poisson's ratio, and t is the thickness of the diaphragm. Thus, it is estimated that a 12.5 micron thick diaphragm with E=1 MPa having a radius of 1 mm and v=0.3 will experience a deflection of 39 microns for a P=2.5 Pa and a deflection of 140 microns for P=100 Pa. Alternatively, one could construct a thicker diaphragm with etched patterns provided to lower the effective spring constant, as desired.

Using materials with a lower Young's modulus will allow for the use of a thicker diaphragm. Suitable materials for use in the diaphragm include metals, as well as plastics and elastomers such as acrylic and silicone elastomers. E for most common metals ranges from about 45 GPa to 200 GPa. When using such a material, the thickness of the diaphragm might range, e.g., from about 20 nm to 300 nm. Typical plastics may have E ranging from about 100 MPa to 4.5 GPa. Diaphragms made from such materials may have a corresponding greater thickness than metal ones. An exemplary class of elastomers suitable for use as the diaphragm include those used in the industry as electroactive polymers (EAP) and described by R. Pelrine, R. Kornbluh, Q. Pei and J. Joseph (Science, vol. 287, pp. 836-839, Feb. 4, 2000). These include VHB 4910 acrylic (from 3M Corporation of Minneapolis, Minn.), HS3 silicone (from Dow Corning of Midland, Mich.), and CF 19-2186 silicone (from NuSil Technology of Carpenteria, Calif.). Such electroactive polymers have typical E values in the range of about 0.3 MPa to 10 MPa. Although not intended to be limiting, diaphragms made from such materials may have typical thicknesses from about 1 to about 50 μm.

Applicants have found that, for reactions in which the reactants are present in the above concentrations, the use of a diaphragm with an effective spring constant of from approximately 0.1 N/m to approximately 2.5 N/m—assuming an area of deflection of the diaphragm of at least approximately 50 µm²—allows for a linear deflection that may be adequately measured. An exemplary range of linear deflection for the diaphragm that may be easily measured is from about 0.025 µm to 200 µm. For such spring constants and an area of deflection of 100 µm², the corresponding linear deflections are shown in Table 1.

TABLE 1

| Spring Constant | Osmotic Pressure | |
| --- | --- | --- |
| | $\pi = 2.5$ N/m² | $\pi = 100$ N/m² |
| k = 0.1 N/m | 0.25 µm | 10 µm |
| k = 1.0 N/m | 0.025 µm | 1 µm |

Figure 3:
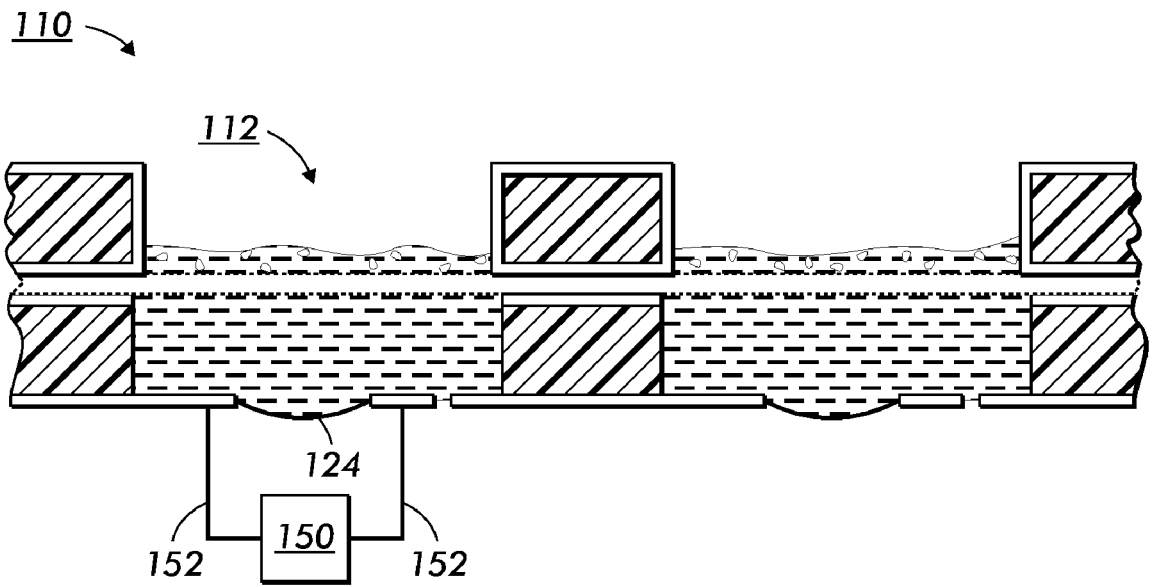
FIG. 3 is a side view of an array of osmotic reaction cells according to a second embodiment.

The deflection of the diaphragm is measured using several techniques, which may be applied to each reaction cell of an array. In one exemplary method, the change of deflection of the diaphragm is measured by a change in capacitance. With reference to FIG. 3, a sensor 110 including one or more osmotic reaction cells 112 as previously described is shown. To measure the deflection of the flexible diaphragm 124 of each reaction cell, a capacitance detector 150 is connected across the diaphragm by two lead wires 152. A deflection in the diaphragm causes a change in capacitance. That is, the change in area of the diaphragm due to the osmotic pressure differential in the two wells causes a change in the capacitance across the diaphragm. Frequency-based measurements of the capacitance may be used to lower the noise in the signal, and sensors in separate control and screening samples can be joined in one circuit to enable common mode rejection. To enable it to function as a capacitor, the flexible diaphragm is preferably coated on both sides with a conductive material as is known in the art.

Figure 4:
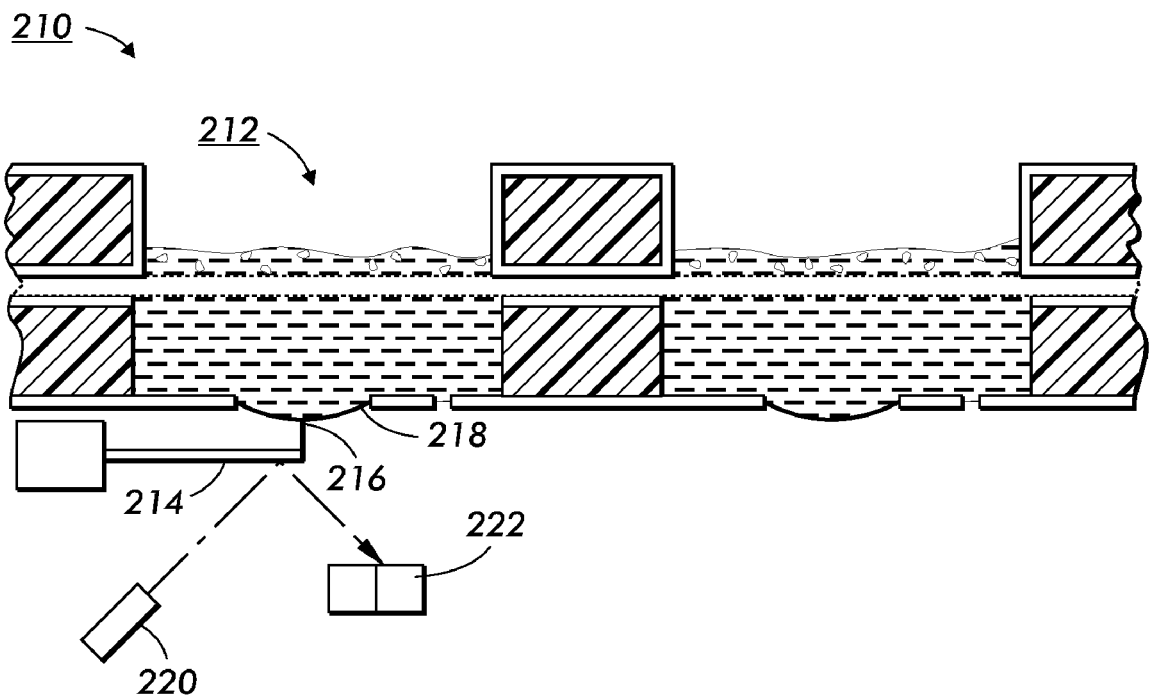
FIG. 4 is a side view of an array of osmotic reaction cells according to a third embodiment.

In another embodiment, the deflection of the diaphragm is measured using a cantilever detector system, similar in principle to those used in atomic force microscopes. Thus, with reference to FIG. 4, a sensor 210 including one or more reaction cells 212 as previously described is shown. A cantilever including an arm 214 and a tip 216 is positioned such that the tip 216 is in contact with the flexible diaphragm 218. The tip 216 moves with the diaphragm 218, following the deflection of the diaphragm, if any. The reflection of a light source 220 off of the cantilever varies with the movement of the cantilever, and is reflected onto a detector 222, which, when calibrated, is used to measure the magnitude of deflection of the diaphragm to thereby determine osmotic pressure changes. The light source may be a laser, diode or other appropriate light-emitting device, and the detector may be a split-diode detector, or other detector, which will perform the required detection of the movement of the reflected light. Movement of the cantilever may also be detected by measuring capacitance changes in the cantilever, as well as changes in resonance of the cantilever as a function of deflection.

Figure 5:
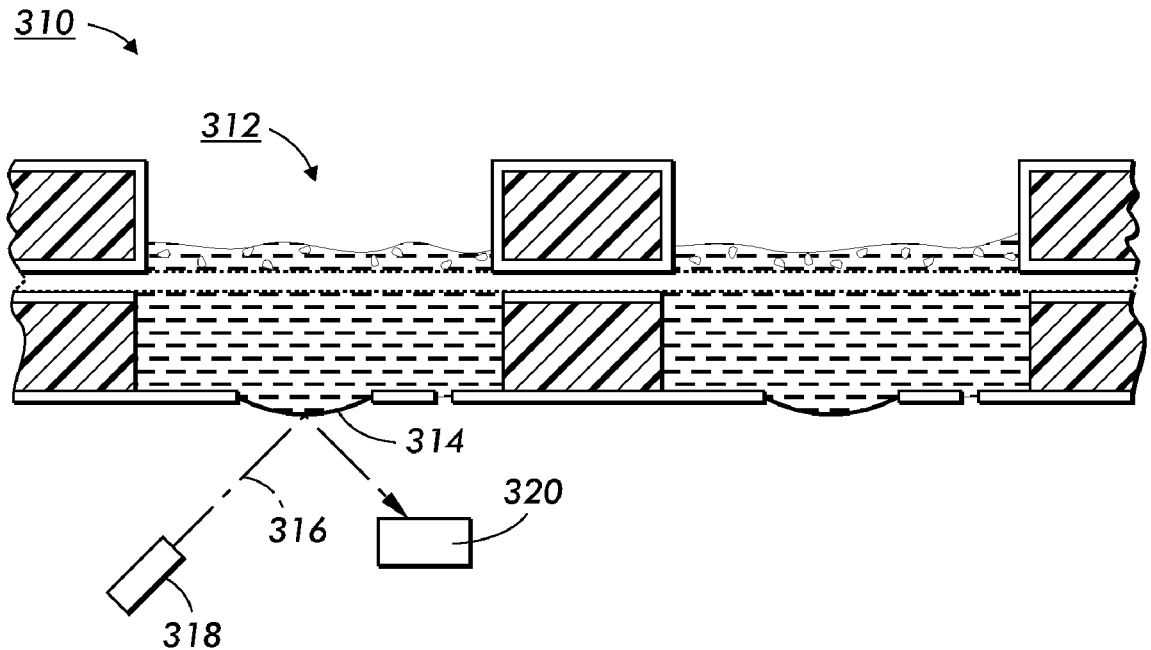
FIG. 5 is a side view of an array of osmotic reaction cells according to a fourth embodiment.

In still another embodiment, the deflection of the diaphragm is measured by observing a reflected light directly from the diaphragm. With reference to FIG. 5, a sensor 310 including one or more reaction cells 312 as previously described is shown. A change in shape of the diaphragm 314 alters the angle of reflection of a light 316 from a light source 318 impacting on the diaphragm, which may be detected by a detector 320. This change in the angle of reflection is correlated to the magnitude of deflection of the diaphragm 314. The light source and detector may be such as those described in relation to FIG. 4. Of course, additional means for measuring the deflection of the diaphragm are possible.

Figure 6:
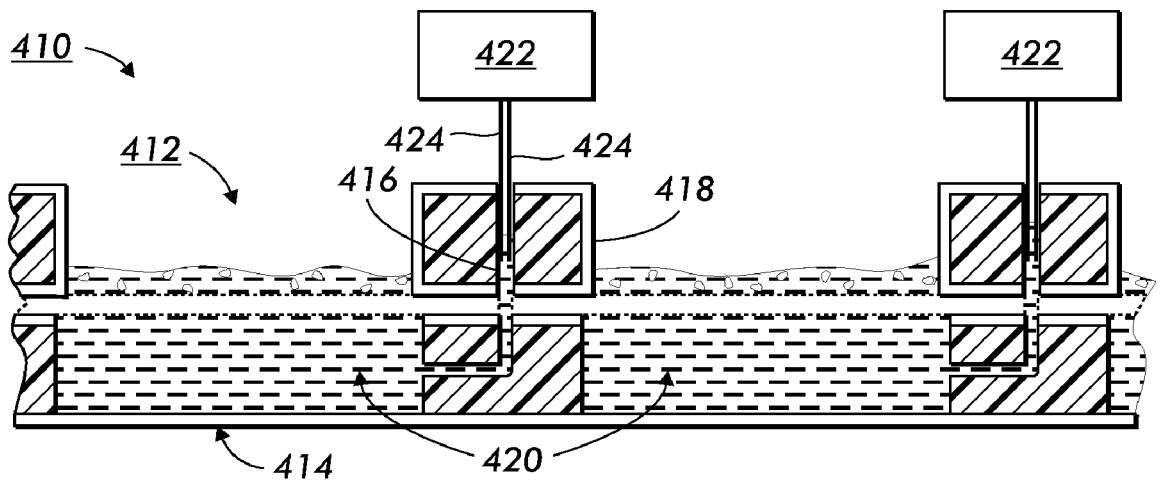
FIG. 6 is a side view of an array of osmotic reaction cells according to a fifth embodiment.

With reference next to FIG. 6, in an alternative arrangement, a sensor 410 includes one or more reaction cells 412 as previously described. In the embodiment illustrated, a solid lower surface 414 is provided as shown. In addition, integral manometers 416 are built into one of the walls 418 of the reaction cells 412 and are in fluid contact with the first wells 420 to measure changes in osmotic pressure in the associated first wells 420.

In this embodiment, the first and second wells are filled as described in the previous embodiments. Prior to any reaction between the antibody and antigen species in the second wells, the solution in the first wells 414 flows into the manometers 416 to an equilibrium height. A change in the osmotic pressure in the first wells due to a reaction between the antibody and the antigen thereafter results in a change in height of solution in the manometer. This change in height is detectable through various processes and indicates that a reaction between the antibody and antigen has occurred.

With further reference to FIG. 6, one preferred procedure for measuring the change in solution height in the manometer is through the use of an electrical probe including a resistance detector 422 and two spaced apart conductors 424 immersed in the liquid in the manometer 416. The resistance between the conductors changes with the liquid height and is monitored. Based on these resistance readings, a change in height of the liquid in the manometer is then recorded. The electrical resistance being measured can be either an AC or DC impedance, using methods known in the art.

Figure 7:
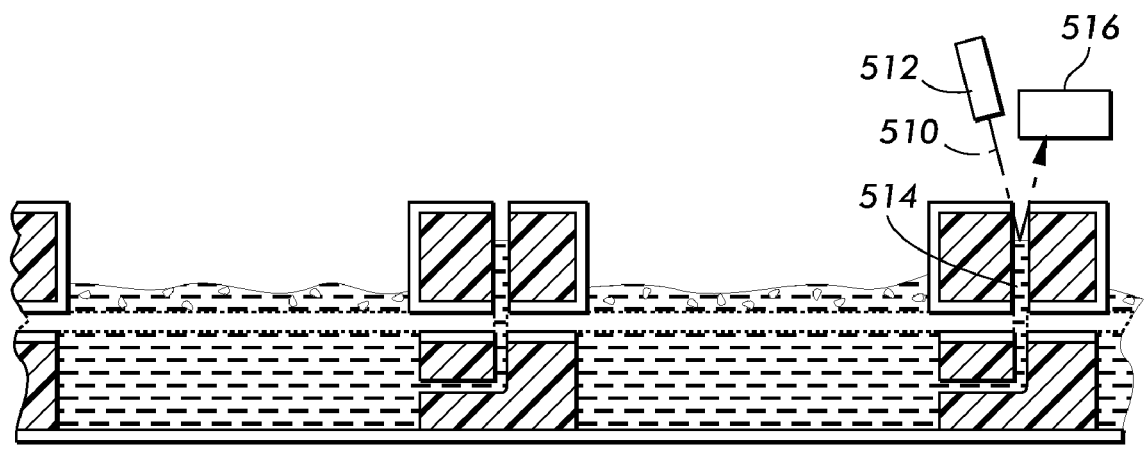
FIG. 7 is a side view of an array of osmotic reaction cells according to a sixth embodiment.

Another procedure which may also be used to measure the change in solution height in the manometer is shown in FIG. 7. The solution height is monitored by shining a light 510 from a light source 512 across manometer 514, at a critical fluid height and detecting the movement of a fluid meniscus. The light 510 may be detected at detector 516 such that the meniscus movement is observable. Still other optical, electrical, or other techniques for monitoring the height of the fluid in the manometer may also be used as understood. The light source and detectors may be among those known in the art.

One advantage of the previous two embodiments and similar embodiments is that the array of reaction cells is manufactured easily and inexpensively without the need for integrating a flexible sensing diaphragm into the arrays. Rather, in the previous two embodiments the sensing elements are separable from the array of reaction cells, allowing them to be used with multiple arrays. Accordingly, a larger cost for the sensing elements is more easily tolerated, and the array of reaction cells can be considered disposable. Also when the array of reaction cells may be discarded after an experiment, the need to clean the cells, including the semi-permeable membranes therein, can be eliminated.

Figure 8:
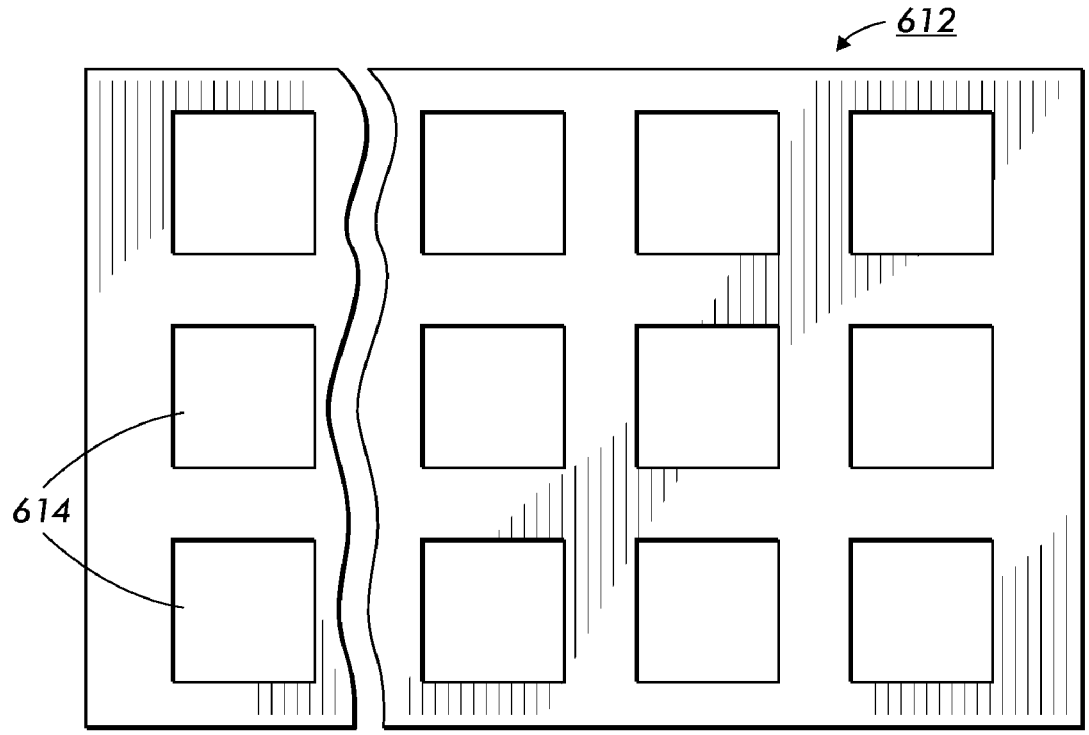
FIG. 8 is a top view of an array of osmotic reaction cells.

Expanding upon the array concepts described herein, reference is made to FIG. 8, which illustrates an array 612 of individual reaction cells 614 according to any one of the embodiments discussed above. Such an array allows for the testing of a large number of samples using the same or different materials of interest and probe compounds in individual reaction cells. Therefore, it is possible to not only perform massive parallel investigations, which is very beneficial for use in areas which employ combinatorial chemistry, but it is also possible to perform distinct investigations by filling reaction cells of the array with distinct solutions and/or reaction mixtures.

Figure 9:
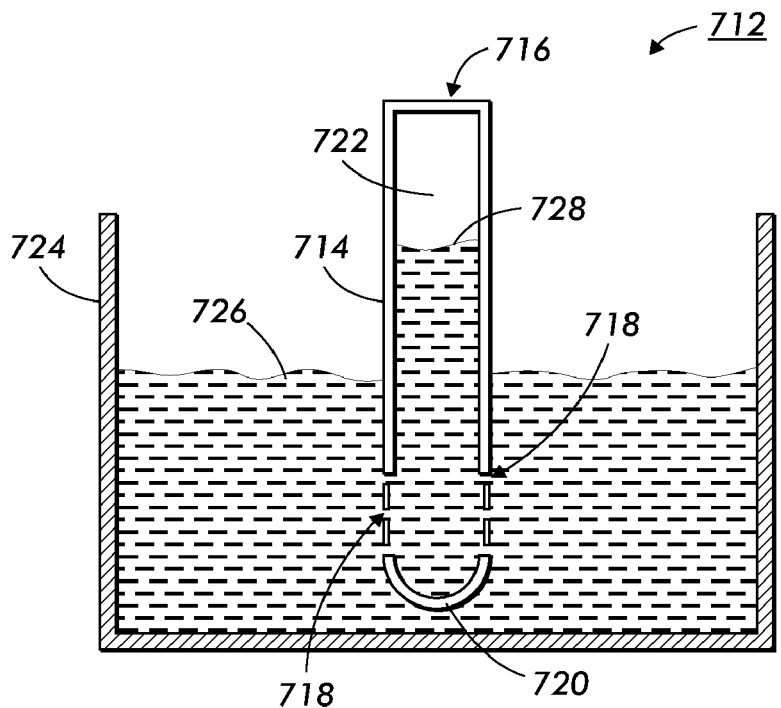
FIG. 9 is a side view of an osmotic reaction detector.

With reference to FIG. 9, in another embodiment, an osmotic reaction detector 712 is shown. The osmotic reaction detector 712 includes a side wall 714 and a top 716. A semipermeable membrane 718 forms at least a part of the side wall 714. A flexible diaphragm 720 is fabricated into or otherwise attached to a bottom of the osmotic reaction detector 712. Of course, the exact placement of the semi-permeable membrane 718 and the flexible diaphragm 720 in the osmotic reaction detector are not critical and should not be thought of as being limited to their location depicted in FIG. 9. The side wall 714 may be a continuous side wall when the osmotic reaction detector 712 is formed with a circumference, and side wall 714 may be configured by a number of side wall portions when the osmotic reaction detector is of other geometric shapes. Top 716 may be a permanently attached top wall with a sealable inlet for provision of fluid into the interior 722. Alternatively, top 716 may be a cap attached after fluid has been introduced. The semi-permeable membrane 718 separates an interior 722 of the osmotic reaction detector 712 from exterior environment 724, which may be a reservoir of fluid 726 such that the semi-permeable membrane 718 is positioned between the fluid 726 in the reservoir 724 and a fluid 728 contained in the osmotic reaction detector. In certain uses, the fluids may be the solution 32 or reactive mixture 34.

Figure 10:
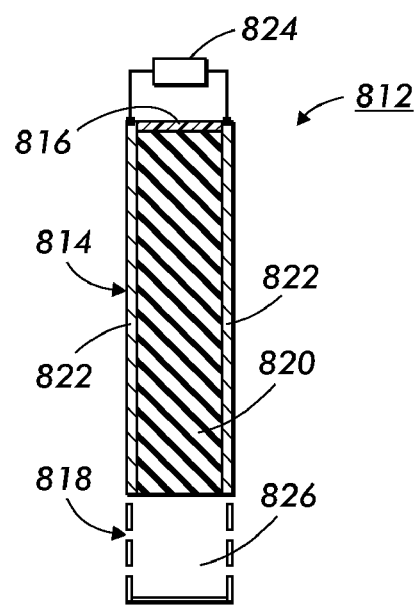
FIG. 10 is a side view of an osmotic reaction detector according to another embodiment.

In another embodiment, and with reference to FIG. 10, an osmotic reaction detector 812 includes side wall 814, top 816 and semi-permeable membrane 818 as in FIG. 9. Then, instead of a flexible diaphragm as a pressure sensing element, this embodiment employs a pressure sensitive gel 820 between two spaced apart conductors 822 in operative connection with a resistance detector 824.

In this embodiment, gel 820 responds to changes in osmotic pressure by contracting or expanding. The gel 820 is designed to have a conductance that depends on compression, making it possible to monitor the amount of expansion or compression, and therefore the osmotic pressure, by measuring the resistance across electrodes 822. As an example of such a gel, one can use a polymer gel material and load it with carbon black particles near the percolation threshold for the particulate phase. Elastomeric materials loaded with conductive particles near their percolation threshold exhibit a conductance having a strong dependence on the applied pressure, this dependence arising because compression increases the number of particle-particle contacts. Conductive particles other than carbon black can be used. Preferably, the polymer gel is made from a material that is not soluble, or only slightly soluble, in the fluids being tested, as a gel that is largely or completely swollen in the fluids being tested will remain completely swollen at different osmotic pressures, eliminating the change in shape with osmotic pressure that is required for this embodiment.

As shown in FIG. 10, gel 820 is arranged wherein conductors 822 are isolated from any of the fluid 826. By this arrangement, the resistance detector 824 will detect changes only due to gel 820. In this respect, the conductors 822 may be separated from the fluid 826 by a non-conductive ring or collar (not shown) with the gel extending between the conductors at a height even with the bottom of the conductors.

Figure 11:
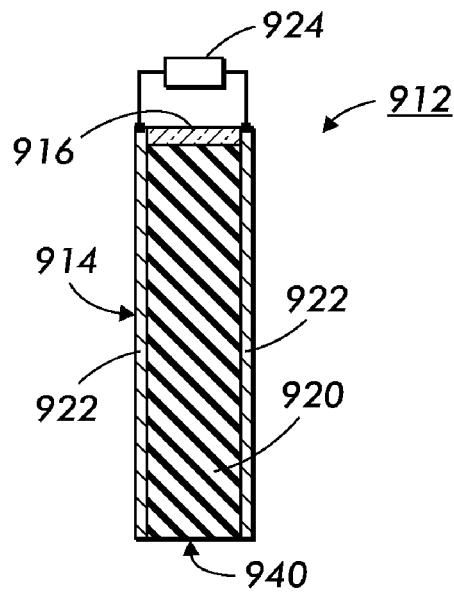
FIG. 11 is a side view of an osmotic reaction detector according to still another embodiment.

With reference to FIG. 11, in another embodiment, an osmotic reaction detector 912 includes side wall 914, and top wall 916 as in FIG. 10. Like the embodiment of FIG. 10, this embodiment also employs a pressure sensitive gel 920 between two spaced apart conductors 922 in operative connection with a resistance detector 924 and exposed directly to a reaction mixture at an interface surface 940. In this embodiment, however, the gel 920 is used as both a semipermeable membrane and a pressure sensitive element. The gel material is chosen such that it partially swells in the carrier fluid of the reaction mixture. (In FIG. 10, such swelling is to be minimized or eliminated.) The gel in FIG. 11 is crosslinked enough that the reactants, for example an antigen and antibody, cannot penetrate the gel. In this case, the osmotic pressure difference between the surface of the gel and its interior will compress the gel. As in the previous embodiment, suitable gels will be designed to have a conductance that depends on compression, making it possible to monitor the amount of compression or expansion, and therefore the osmotic pressure, by measuring the resistance across electrodes 922. It should be noted that the osmotic pressure in this embodiment is not the osmotic pressure of an antibody-antigen reaction mixture at concentration N for both components relative to a solution at concentration 2 N in one component, as the antibody and antigen cannot penetrate the gel.

Figure 12:
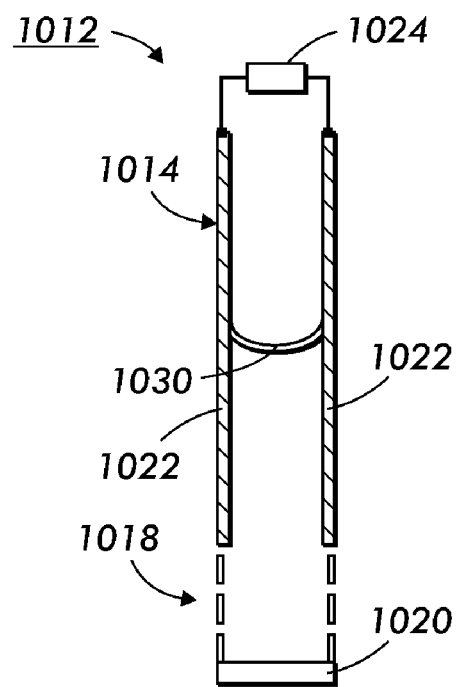
FIG. 12 is a side view of an osmotic reaction detector according to yet another embodiment.

With reference to FIG. 12, in another embodiment, an osmotic reaction detector 1012 includes side wall 1014, and semi-permeable membrane 1018 as in FIGS. 9 and 10. In this embodiment, the reaction detector is filled to a fluid height 1030. Also, instead of a flexible diaphragm as a pressure sensing element, this embodiment has a solid bottom surface 1020, and uses an electrical probe including two spaced apart conductors 1020 immersed in the fluid below the fluid height 1030 in the reaction detector, and connected to a resistance detector 1024. The resistance between the conductors 1020, which will vary with the liquid height 1030, is then monitored. Based on these resistance readings, a change in height of the liquid in the cell may be monitored. In one embodiment the fluid heights corresponding to pressures of 2.5 Pa to 100 Pa are 0.25 mm to 10 mm, which are well within a measurable range. This design provides a benefit of using a well controlled physical property (i.e., measuring capillary rise). It is understood, that to address stiction caused by fluid wall interaction, the surface properties of the interior walls need to be appropriately selected and controlled.

Figure 13:
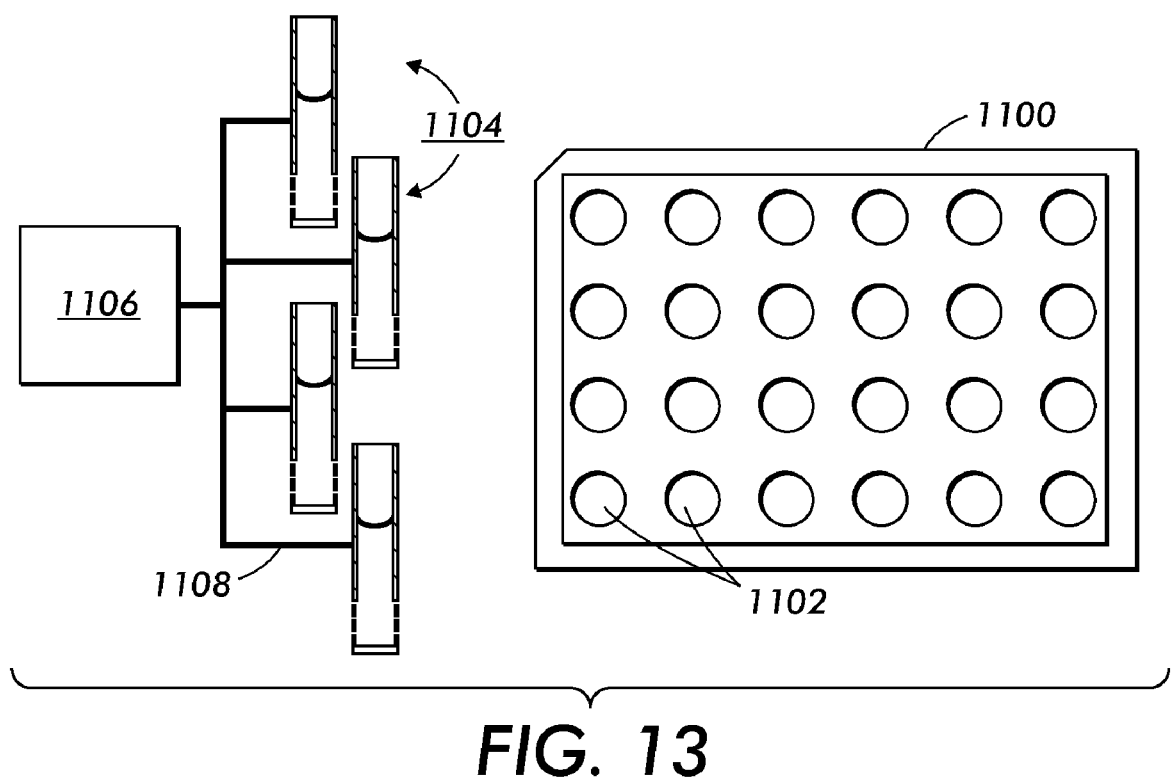
FIG. 13 shows top and perspective views of an array of osmotic reaction detectors moved by a robotic system and a titer plate.

A reaction detector as described in these embodiments allows for the testing of a large number of samples using a titer plate into which a solution or reactive mixture has been introduced. Thus, as shown in FIG. 13, a well plate (e.g., titer plate) 1100 containing a plurality or array of wells 1102, into which solutions of reactive mixtures have been introduced is provided. A plurality or array of osmotic reaction detectors 1104 according to any of the embodiments described in FIGS. 9-11, having appropriate solutions or reactive mixtures, are then selectively placed in the wells 1102, preferably by automated means such as a robotic arm 1108 maneuvered by a control system 1106. The reactive detectors are placed into the wells to a position where osmotic processes will occur. In this way, a large number of samples may be tested at a single time. Benefits of using a plurality of osmotic reaction detectors in parallel include a decrease required testing time and the capability of performing different investigations simultaneously. Specifically, by loading the osmotic reaction detectors with different fluids, individual osmotic reaction detectors can perform investigations which are distinct from investigations of other ones of the osmotic reaction detectors in the array. Of course in an alternative design, the robotic arm 1108 may carry a single osmotic reaction detector 1104 which it may move from well to well.

The exemplary embodiment has been described with reference to the disclosed embodiments. Obviously, modifications and alterations will occur to others upon reading and understanding the preceding detailed description. It is intended that the exemplary embodiments be construed as including all such modifications and alterations insofar as they come within the scope of the appended claims or the equivalents thereof.

The invention claimed is:

1. An osmotic cell system for monitoring reactivity in reactions between a first material of interest and a second material of interest, said osmotic cell system comprising:
a first well for containing a reference solution;
a second well having substantially the same physical dimensions as the first well and for containing a reaction mixture comprising at least first and second materials of interest;
a semi-permeable membrane separating said first well from said second well; and
a pressure sensor for measuring changes in osmotic pressure in said first well and said second well after allowing said first and second wells to reach equilibrium, wherein said pressure sensor is a deflectable diaphragm operatively associated only with the first well containing the reference solution.

2. An osmotic cell system according to claim 1, wherein said diaphragm has an effective spring constant of from 0.1 to 2.5 N/m$^2$.

3. An osmotic cell system according to claim 1, wherein said diaphragm has an E modulus of 0.3 MPa to 200 Gpa.

4. An osmotic cell system according to claim 1, wherein said diaphragm has a linear deflection of from approximately 0.025 μm to approximately 200 μm.

5. An osmotic cell system according to claim 1, wherein said first and second wells have a volume of from approximately 0.05 μl to approximately 100 μl.

6. An osmotic cell system according to claim 1, wherein said semi-permeable membrane has molecular weight cutoffs ranging from 100 Dalton to 300,000 Dalton.

7. An osmotic cell system according to claim 1, wherein said deflectable diaphragm comprises an electroactive polymer.

8. An osmotic cell system according to claim 1, wherein said first and second materials of interest are at an initial concentration in said reaction mixture in the range of approximately $5\times10^{-5}$M to $5\times10^{-7}$M.

9. An osmotic cell system according to claim 1, wherein said pressure sensor measures changes in osmotic pressure in a range of approximately 1.2 N/m$^2$ to 130 N/m$^2$.

10. An osmotic cell system according to claim 1, wherein said system comprises an array of osmotic cells and at least two of the osmotic cells of the array utilize different first and/or second materials.

11. An osmotic cell system according to claim 10, wherein said at least two osmotic cells are monitored simultaneously.

12. An osmotic cell system according to claim 1, wherein said system further includes a light source operatively associated with said diaphragm and deformation of said deflectable diaphragm is measured by a change in deflection of light from said light source incident on said diaphragm.

13. An osmotic cell system according to claim 1, wherein said system further includes a cantilever operatively associated with said diaphragm and deformation of said deflectable diaphragm is measured by a change in deflection of said cantilever.

14. An osmotic cell system according to claim 1, wherein at least one of said first or second materials of interest is an antibody, an antigen, a nucleic acid, a oligonucleotide, a polypeptide, a protein, or a ligand.

15. An osmotic cell system according to claim 1, wherein an initial molar concentration of solute molecules in said reference solution is equal to the combined initial molar concentration of said first and second materials of interest in said reaction mixture.

16. An osmotic cell system according to claim 1, wherein said reference solution comprises any one or combination of the first material of interest, the second material of interest, a surrogate reference material and a carrier fluid.

17. An osmotic cell system according to claim 16, wherein said semi-permeable membrane is impermeable to said first and second materials of interest and said surrogate reference material and is permeable to said carrier fluid.

18. An osmotic cell system according to claim 16, wherein said semi-permeable membrane is impermeable to at least one of said first material, said second material and said surrogate reference material, and is permeable to at least one of said first material and said second material and said surrogate reference material or products of a reaction between said first material and said second material.

* * * * *